(12) United States Patent
Chen et al.

(10) Patent No.: US 9,150,896 B2
(45) Date of Patent: Oct. 6, 2015

(54) NUCLEOTIDES AND PRIMERS WITH REMOVABLE BLOCKING GROUPS

(71) Applicant: Illumina, Inc., San Diego, CA (US)

(72) Inventors: Cheng-Yao Chen, San Diego, CA (US); Gothami Padmabandu, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 125 days.

(21) Appl. No.: 13/782,066

(22) Filed: Mar. 1, 2013

(65) Prior Publication Data

US 2014/0065675 A1 Mar. 6, 2014

Related U.S. Application Data

(60) Provisional application No. 61/697,669, filed on Sep. 6, 2012.

(51) Int. Cl.
*C12Q 1/68* (2006.01)
*C12P 19/34* (2006.01)

(52) U.S. Cl.
CPC ............. *C12P 19/34* (2013.01); *C12Q 1/6848* (2013.01)

(58) Field of Classification Search
CPC .................................................... C12Q 1/6876
See application file for complete search history.

(56) References Cited

U.S. PATENT DOCUMENTS

| 7,057,026 B2 | 6/2006 | Barnes et al. |
| 7,541,444 B2 * | 6/2009 | Milton et al. .................. 536/4.1 |
| 7,566,537 B2 | 7/2009 | Barnes et al. |
| 8,158,346 B2 | 4/2012 | Balasubramanian et al. |
| 2007/0166705 A1 | 7/2007 | Milton et al. |
| 2007/0281308 A1 | 12/2007 | Zon et al. |
| 2010/0003724 A1 | 1/2010 | Lebedev et al. |

FOREIGN PATENT DOCUMENTS

| WO | WO 2007/139723 A1 | 12/2007 |
| WO | 2008/037568 | 4/2008 |
| WO | WO 2009/151921 A1 | 12/2009 |
| WO | WO 2014/039225 A1 | 3/2014 |

OTHER PUBLICATIONS

Lebedev, A. et al., "Hot Start PCR with heat-activatable primers: a novel approach for improved PCR performance", Nucleic Acids Research, vol. 36, No. 20 e131, Sep. 16, 2008, 18 pages.
ISA, International Search Report dated Mar. 13, 2014 for International Application No. PCT/US13/55065.
Koukhareva, I. et al.,"Heat activatable 3'-modified dNTPs: synthesis and application for Hot Start PCR", Nucleic Acids Symposium Series, vol. 52, No. 1, pp. 259-260, Sep. 1, 2008.

\* cited by examiner

*Primary Examiner* — Kenneth R. Horlick
*Assistant Examiner* — David Thomas
(74) *Attorney, Agent, or Firm* — Jones Day (57) ABSTRACT

Provided herein is a method of amplifying nucleic acids using a plurality of modified nucleotides one or more of the nucleotides comprising a 3' blocking group. Also provided is a method of amplifying nucleic acids using oligonucleotide primers one or both of the primers comprising a 3' blocking group on one or more of the nucleotides of the primers.

50 Claims, 5 Drawing Sheets

NUCLEOTIDES AND PRIMERS WITH REMOVABLE BLOCKING GROUPS

The present application claims priority to U.S. provisional patent application Ser. No. 61/697,669 filed on Sep. 6, 2012, which is incorporated herein by reference in its entirety.

BACKGROUND

Polymerase Chain Reaction (PCR) is highly important in the field of molecular biology through its ability to identify, manipulate and reproduce genetic material such as DNA. PCR is routinely performed in a variety of medical and research laboratories, for example, to detect and/or identify disease and clone genes. PCR involves heating and cooling genetic material in the presence of, at least, target specific PCR primers, and one or more thermostable polymerases, in order to amplify one or more desired targets within the genetic material. However, amplification of non-specific sequences by mis-priming of the PCR primers can compete with amplification of the desired target sequences and reduce amplification efficiency of the target. To reduce nonspecific product amplification or mis-priming of PCR primers, techniques referred to as "hot-start" PCR have been developed. General hot-start PCR strategies include the use of temperature sensitive materials that prevents mixing of reagents until the appropriate time or temperature sensitive polymerases that have been modified to become active at a certain temperature. The most common hot-start strategies involve the use of oligonucleotide aptamers or antibodies that inhibit the function of DNA polymerase or chemically modified polymerases with reversible modifications. Other hot-start PCR strategies include the use of oligonucleotide primer sequence constructs that disfavor mis-priming, such as competitor sequences.

SUMMARY

Provided herein is a method of amplifying nucleic acids using a plurality of modified nucleotides one or more of the nucleotides comprising a 3' blocking group. Also provided is a method of amplifying nucleic acids using a oligonucleotide primers one or both of the primers comprising a 3' blocking group on one or more of the nucleotides of the primers.

The details of one or more embodiments are set forth in the accompanying drawings and the description below. Other features, objects, and advantages will be apparent from the description and drawings, and from the claims.

DESCRIPTION OF DRAWINGS

FIGS. 4A and 4C are graphs showing qPCR amplification using modified nucleotides comprising 3' blocking groups. FIGS. 4A and 4C; Y axis is change is fluorescence (dRn) from −0.1 to 1.2. X axis is number of cycles from 0 to 40. FIGS. 4 B and D; Y axis is change in fluorescence (dRn) from −0.1 to 1.2; X-axis is temperature (° C.) from 55 to 95.

DETAILED DESCRIPTION

Provided herein is a method of amplifying nucleic acids including the steps of providing a plurality of modified nucleotides one or more of the nucleotides comprising a 3' blocking group, removing the 3' blocking groups, and amplifying the nucleic acids. Optionally, the plurality of modified nucleotides can comprise one, two, three, four or more types of modified nucleotides. Optionally, the four types of modified nucleotides can be dATP, dGTP, dCTP, and dTTP. The modified nucleotides of the nucleotide bases A, T, C and G are usually recognized as substrates by the same polymerase enzyme. Optionally, the four types of modified nucleotides can be dATP, dGTP, dCTP and dUTP.

Also provided is a method of amplifying a target nucleic acid including the steps of providing a pair of oligonucleotide primers one or both of the primers comprising a 3' blocking group on one or more of the nucleotides of the oligonucleotide primers, removing the 3' blocking group, and amplifying the target nucleic acid using the oligonucleotide primers.

In the provided methods, at least one modified nucleotide comprising a 3' blocking group (i.e., 3' substitution) is used in a reaction comprising nucleic acids to be replicated or amplified. The 3' substitution or 3' blocking group impairs or prevents polymerase extension of a primer. As described above, the 3' blocking group can be located on the nucleotides used to extend the primers or can be located on one or both of the primers themselves. Optionally, the 3' blocking group is not thermolabile. As used herein, the term thermolabile 3' substitution refers to a substitution that is removed by heat (i.e., the 3' substitution is replaced by a 3' hydroxyl group). As used herein, a thermolabile 3' substitution is removed by heat in the absence of enzymes, chemical reagents, and the like. Examples of thermolabile 3' substitutions include those described in U.S. Publication No. 2010/0003724 and 2007/0281308.

When modified nucleotides are used, the modified nucleotides have a 3' blocking group which is unable to be incorporated into an oligonucleotide primer or, alternatively, is incorporated onto the 3' end of an oligonucleotide primer but further extension of the primer is impaired or prevented. The nucleotide with the 3' blocking group is in an inactive state due to the presence of the 3'-substitution or blocking group. Following removal of the 3' blocking group, an inactive nucleotide can be converted to an active state by conversion of the 3'-substitution group to an unmodified or open 3'-OH group. This active state of the nucleotide is the corresponding natural or 3'-unsubstituted nucleotide or functional derivative thereof, which possesses an unsubstituted or open 3'-OH group. The active nucleotide can be a substrate for nucleic acid polymerase and supports nucleic acid replication or amplification. If the 3' blocking group is on one or more nucleotides of a primer, the primer is in an inactive state and is unable to be extended by a nucleic acid polymerase. After removal of the 3' blocking group, the primer can be extended by incorporation of unblocked nucleotides by a nucleic acid polymerase.

The modified nucleotide provided herein may be used in conjunction with one or more other hot start methods and compositions known to those of skill in the art including use of temperature-sensitive materials, such as waxes as barriers or sequestrants to control mixing of the reagents; oligonucleotide aptamers or antibodies that inhibit the function of nucleic acid polymerases; use of a second thermostable enzyme, such as pyrophosphatase to remove suppression by added pyrophosphate (PPi); chemically modified polymerases with hydrolytically reversible reagents, such as citraconic acid-modified lysine; oligonucleotide primer sequence constructs that disfavor low-temperature mis-priming, such as competitor sequences; thermally labile modified nucleotides or primers as described in U.S. Publication No. 2010/0003724 and 2007/0281308; and chemically modified primers containing phosphotriester internucleotide linkage(s) near the 3'-end of the primer (i.e., phosphotriester primers)).

Removal of the 3' blocking group, whether on the primers or modified nucleotides, can occur at any time, as long as the 3' blocking groups are removed prior to amplification. Optionally, the 3' blocking group is removed in the initial denaturation step of the amplification. Optionally, removal of the 3' blocking group results in conversion of the 3' blocking group into a 3' hydroxyl group.

Suitable 3' blocking groups and methods for removing the 3' blocking groups include, but are not limited to, the 3' blocking groups and methods described in U.S. Pat. No. 7,541,444, which is incorporated by reference herein in its entirety. By way of example, suitable 3' blocking groups include, but are not limited to, groups attached to the 3' carbon atom of the modified nucleotide of the structure —O—Z, wherein Z is any of —C($R^{IV}$)$_2$—O—R", —C(R')$_2$—N(R")$_2$, —C(R')2-N(H)R", —C($R^{IV}$)$_2$—S—R" and —C(R')$_2$—N$_3$; wherein —C($R^{IV}$)$_2$—O—R" is of the formula —C$R^4$($R^5$)—O—C$R^4$($R^5$)—O$R^6$ or of the formula —C$R^4$($R^5$)—O—C$R^4$($R^5$)—S$R^6$, and wherein —C($R^{IV}$)$_2$—S—R" is of the formula —C$R^4$($R^5$)—S—C$R^4$($R^5$)—O$R^6$ or of the formula —C$R^4$($R^5$)—S—C$R^4$($R^5$)—S$R^6$;

wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group, or (R')$_2$ represents an alkylidene group of formula =C(R''')$_2$ wherein each R''' may be the same or different and is selected from the group comprising hydrogen and halogen atoms and alkyl groups;

each $R^4$ and $R^5$ is independently a hydrogen atom or an alkyl group;
$R^6$ is alkyl, cycloalkyl, alkenyl, cycloalkenyl or benzyl; and wherein said molecule may be reacted to yield an intermediate in which each R" is exchanged for H, which intermediate dissociates under aqueous conditions to afford a molecule with a free 3'OH; with the proviso that where Z is —C($R^{IV}$)$_2$—S—R", both $R^{IV}$ groups are not H.

Optionally, Z is an azidomethyl group. Optionally, R' is an alkyl or substitute alkyl. R" can be a benzyl or substituted benzyl group.

By way of another example, the 3' blocking group can be a group attached to the 3' carbon atom of the modified nucleotide of the structure —O—Z, wherein Z is selected from the group consisting of -allyl, —CR'$_2$O-allyl, —CR'$_2$NR"(allyl), —CR'$_2$NH(allyl), —CR'$_2$N(allyl)$_2$, and —CR'$_2$—S-allyl;

wherein each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy, amido group or two R' taken together represent an alkylidene group =C(R)'';

wherein R''' is selected from hydrogen, halogen, and alkyl; and

R" is a removable protecting group.

Such 3' blocking groups can be removed as described in U.S. Pat. No. 7,541,444, which is incorporated by reference herein in its entirety. For example, the 3' blocking group is removed with tris(hydroxymethyl)phosphine (THP). Optionally, the 3' blocking group is removed with tris(2-carboxyethyl)phosphine. Optionally, the blocking group is removed with a composition comprising a transition metal and one or more ligands. Optionally, the ligands are water-soluble phosphine ligands or water-soluble nitrogen-containing phosphine ligands. Optionally, Z is an allyl group and the blocking group is removed in aqueous solution with a transition metal complex comprising a transition metal and one or more phosphine ligands.

Suitable transition metals for use in the provided methods include, but are not limited to, platinum, palladium, rhodium, ruthenium, osmium and iridium. The transition metal, e.g. palladium, can be introduced as a salt, e.g. as a halide. Mixed salts such as Na$_2$PdCl$_4$ may also be used. Other appropriate salts and compounds will be readily determined by the skilled person and are commercially available, e.g. from Sigma-Aldrich (Milwaukee, Wis.).

Suitable ligands for use in the provided methods include, but are not limited to, water-soluble phosphine or nitrogen-containing phosphine ligands. Suitable phosphine ligands include, but are not limited to, derivatized triaryl phosphine ligands or derivatized trialkyl phosphine ligands. Optionally, the phosphine ligands are derivatized with one or more functionalities selected from the group comprising amino, hydroxyl, carboxyl and sulfonate groups. Optionally, the ligands can be 3,3',3"-phosphinidynetris(benzenesulfonic acid), tris(2-carboxyethyl)phosphines and their salts.

The water-soluble phosphines and nitrogen-containing phosphines described herein may be used as their salts (e.g. as the hydrochloride or sodium salts) or, for example, in the case of the sulfonic and carboxylic acid-containing phosphines described herein, as the free acids. Thus, 3,3',3"-phosphinidynetris(benzenesulfonic acid) and tris(2-carboxyethyl) phosphines may be introduced either as the triacids or the trisodium salts. The choice of salt or salt form is not particularly important provided the phosphines are soluble in an aqueous solution.

The term blocking group includes, but is not limited to, the blocking groups described herein. When mixtures of nucleotides are used, each nucleotide or type of nucleotide can comprise the same type of blocking group or a different blocking group. For example, in a mixture of nucleotides comprising A, G, T, and C, the As can comprise one type of blocking group, while the Ts can comprise a different type of blocking group. Thus, each type of nucleotide can comprise a different blocking group (i.e., A comprises a first blocking group, G comprises a second blocking group, T comprises a third blocking group, and C comprises a fourth blocking group). Alternatively, a plurality of one type of nucleotides (e.g., As or Gs) can comprise one, two, three, four, or more types of blocking groups. Likewise, more than one ligand and, optionally, transition metal can be used in the provided methods according to the specific blocking groups on the modified nucleotide. For example, if a first block is on A and a second block is on C then a first ligand (and, optionally, transition metal) can be used to remove the second block and the second block can be removed with the first ligand or a second ligand (and, optionally, a second transition metal).

One or both of the primers can comprise a detectable label. Detectable labels include any substance which is capable of producing a signal that is detectable by visual or instrumental means. Suitable labels include, but are not limited to, labels which produce signals through either chemical or physical means, such as fluorescent dyes, chromophores, electrochemical moieties, enzymes, radioactive moieties, phosphorescent groups, fluorescent moieties, chemiluminescent moieties, or quantum dots.

Optionally, amplification occurs in the presence of a probe. The probe can be, for example, a fluorescent reporter probe. Optionally, the probe is selected from the group consisting of a TaqMan® probe, a MNAzyme, a molecular beacon probe, and a Scorpion™ probe. Methods for performing probe-based quantitative amplification are known. See, for example, U.S. Pat. No. 5,210,015; U.S. Publication No. 2007/0231810; U.S. Pat. No. 5,925,517; and U.S. Pat. No. 6,270,967, which are incorporated by reference herein in their entireties.

Optionally, the amplification occurs in the presence of a nucleic acid binding agent. Nucleic acid binding agents, include, but are not limited to, intercalating agents, major and minor nucleic acid groove binders and nucleic acid stains. Such agents are known and commercially available, e.g., from Molecular Probes, Inc. (Eugene, Oreg.). Optionally, the nucleic acid binding agent is selected from the group consisting of SYBR green, SYBR blue, DAPI, propidium iodine, Hoeste, SYBR gold, and ethidium bromide.

As used herein, the terms replication, replicate, amplification, or amplify refer to methods known by those of skill in the art for copying a target nucleic acid, thereby increasing the number of copies of one or more selected nucleic acid sequences. Replication and amplification involving the compositions and methods provided herein may employ 3'-substituted NTPs and/or primers with nucleic acid polymerase extension. Replication or amplification of target nucleic acid may be exponential, nonlinear or linear. While the exemplary methods described hereinafter relate to PCR amplification, numerous other methods suitable for the methods and compositions provided herein are known in the art for amplification and reproduction of nucleic acids. For example, other enzymatic replication and amplification methods include isothermal methods, rolling circle methods, Hot-start PCR, real-time PCR, Allele-specific PCR, Assembly PCR or Polymerase Cycling Assembly (PCA), Asymmetric PCR, Colony PCR, Emulsion PCR, Fast PCR, Real-Time PCR, nucleic acid ligation, Gap Ligation Chain Reaction (Gap LCR), Ligation-mediated PCR, Multiplex Ligation-dependent Probe Amplification, (MLPA), Gap Extension Ligation PCR (GEXL-PCR), quantitative PCR (Q-PCR), Quantitative real-time PCR (QRT-PCR), multiplex PCR, Helicase-dependent amplification, Intersequence-specific (ISSR) PCR, Inverse PCR, Linear-After-The-Exponential-PCR (LATE-PCR), Methylation-specific PCR (MSP), Nested PCR, Overlap-extension PCR, PAN-AC assay, Reverse Transcription PCR (RT-PCR), Rapid Amplification of cDNA Ends (RACE PCR), Single molecule amplification PCR (SMA PCR), Thermal asymmetric interlaced PCR (TAIL-PCR), Touch-down PCR, long PCR, nucleic acid sequencing (including DNA sequencing and RNA sequencing), transcription, reverse transcription, duplication, DNA or RNA ligation, and other nucleic acid extension reactions known in the art. The skilled artisan will understand that other methods may be used either in place of, or together with, PCR methods, including enzymatic replication reactions developed in the future. See, e.g., Saiki, "Amplification of Genomic DNA" in PCR Protocols, Innis et al., eds., Academic Press, San Diego, Calif., 13-20 (1990); Wharam, et al., 29(11) Nucleic Acids Res, E54-E54 (2001); Halher, et al., 30(4) Biotechniques, 852-6, 858, 860 passim (2001); Ross, P., et al., International Patent Appl. No. WO 91/06678; Kwiatkowski, M., U.S. Pat. No. 6,255,475, U.S. Pat. No. 6,309,836, and U.S. Pat. No. 6,639,088 and EP1218391; Anazawa, T., et al., U.S. Pat. No. 6,242,193; Ju, et al., U.S. Pat. No. 6,664,079; Tsien, R. Y., et al., International Patent Appl. No. WO 91/06678; and Dower, et al., International Patent Appl. No. WO 92/10587.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a method is disclosed and discussed and a number of modifications that can be made to the method steps are discussed, each and every combination and permutation of the method steps, and the modifications that are possible are specifically contemplated unless specifically indicated to the contrary. Likewise, any subset or combination of these is also specifically contemplated and disclosed. This concept applies to all aspects of this disclosure. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application various publications, patent and/or patent application publications have been referenced. The disclosure of these publications in their entireties is hereby incorporated by reference in this application in order to more fully describe the state of the art to which this invention pertains.

A number of embodiments have been described. Nevertheless, it will be understood that various modifications may be made. Accordingly, other embodiments are within the scope of the following claims.

EXAMPLES

Example 1

Use of Reversible 3' Terminated Primers for Hot-Start PCR

Experiments were performed to determine the effect of THP on hot start amplification reactions using reversible 3' terminated amplification primers. Briefly, to determine if THP would inhibit the qPCR reaction, varying concentrations of THP were added to a SYBR Green containing qPCR reaction containing reversible 3' terminated amplification primers to two different targets; 1) Factor V target from human genomic DNA, and 2) β-2 microglobulin from cDNA prepared from human qPCR reference RNA (Agilent cat #750500). Bioline Sensimix SYBR Master Mix was used for amplification (Bioline cat #QT650-02). A final concentration of 200 nM of each primer was used in qPCR reactions. Template DNA of 5000 copies of human gDNA or 2.5 ng of cDNA was used in the appropriate reactions. For testing the effect of THP on a hot start qPCR, THP concentrations of 31.25 µM-10 mM in 2-fold increments were tested. A no THP control was included. Cycling parameters were; 95° C. for 10 min (initial enzyme activation) followed by 40 cycles of 95° C. for 15 sec/60° C. for 1 min.

Figure 1:
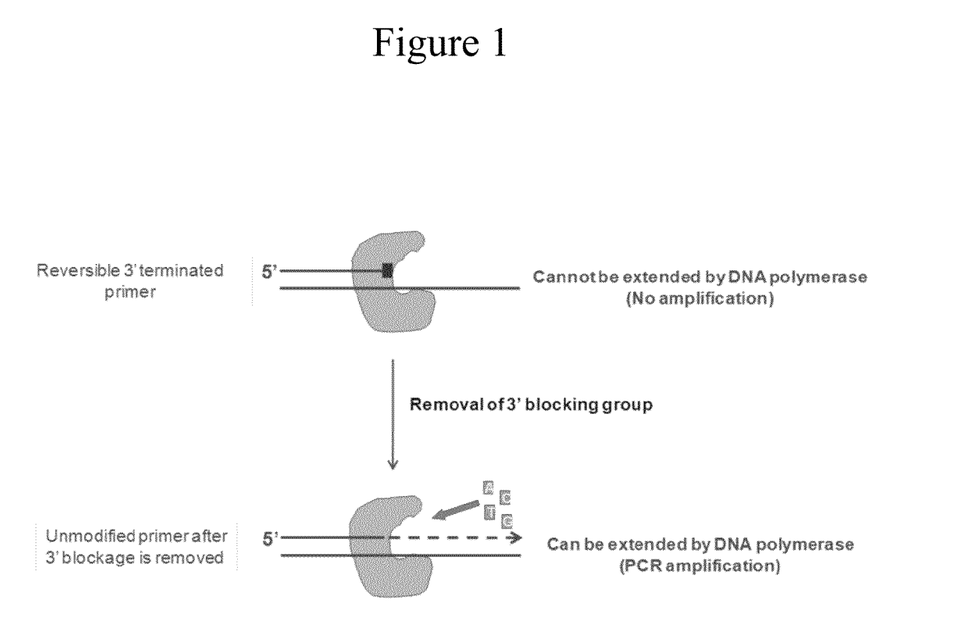
FIG. 1 is a schematic showing use of a 3' terminated primer for hot-start PCR. The presence of a 3' blocking group on the terminating nucleotide on the oligonucleotide primer prevents the DNA polymerase from incorporating nucleotides. To initiate the PCR reaction, the 3' blocking group is removed and amplification proceeds.
Figure 2:
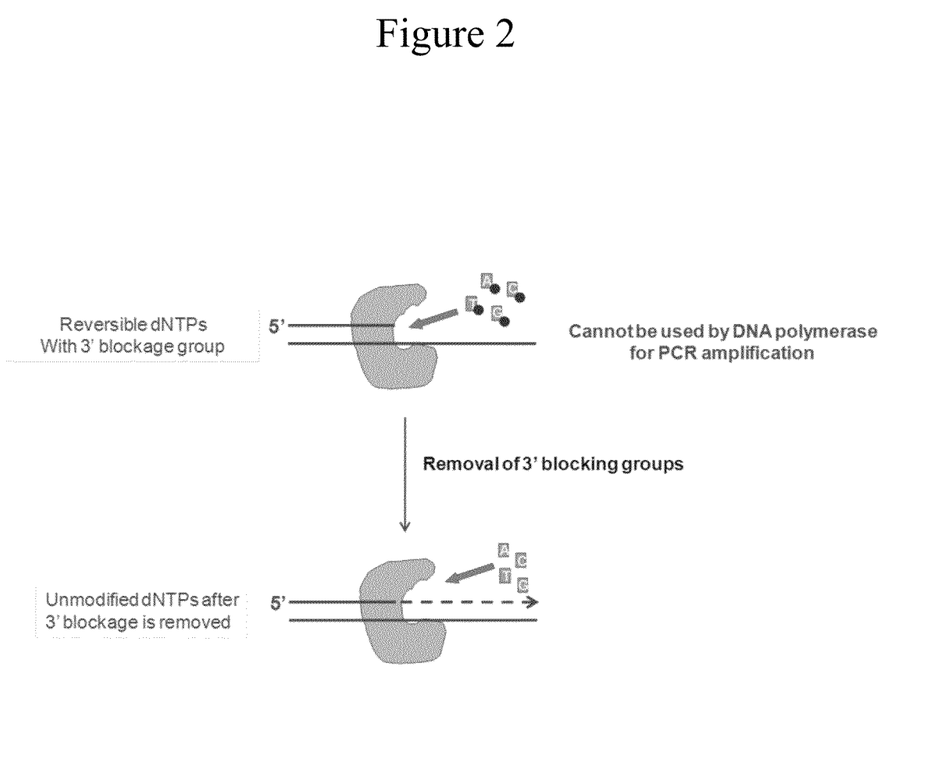
FIG. 2 is a schematic showing use of modified nucleotides comprising 3' blocking groups for PCR. Four nucleotides comprising 3' blocking groups prevent the DNA polymerase from incorporating nucleotides. To initiate the PCR reaction, the 3' blocking groups from the modified nucleotides are removed and amplification proceeds.
Figure 3A:
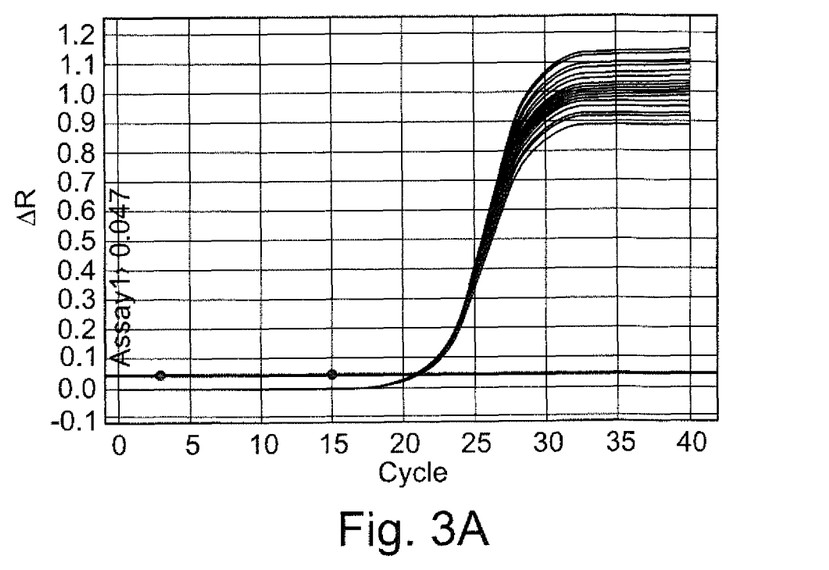
FIGS. 3A and 3B are graphs showing that tris(hydroxymethyl)phosphine (THP) does not inhibit PCR amplification of the Factor V or beta-2 microglobulin genes. Y axis is change is fluorescence (dRn) from −0.1 to 1.2. X axis is number of cycles from 0 to 40.
Figure 3B:
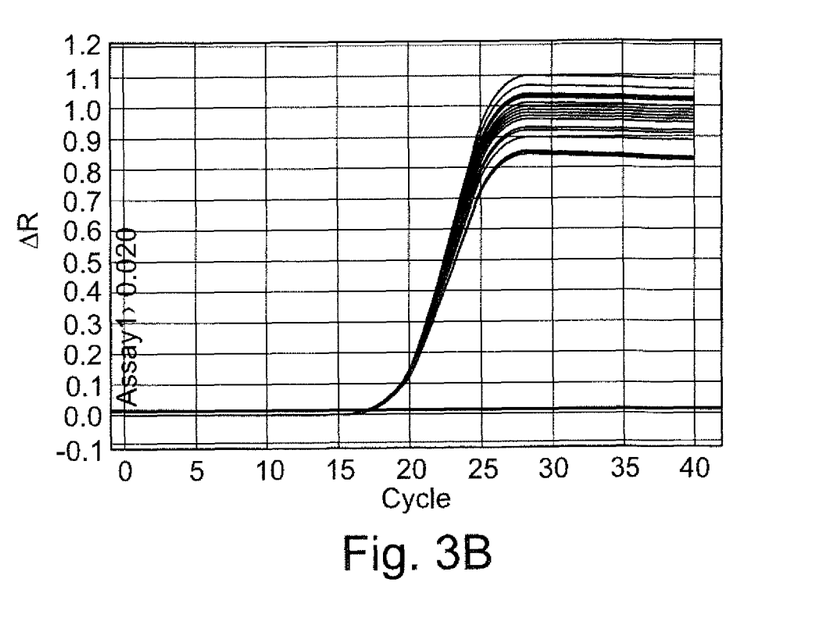

FIGS. 3A and B demonstrate that the THP concentrations being evaluated were well tolerated in qPCR reactions under the experimental conditions. Tables 1 and 2 report representative average Cq for FIGS. 3A and 3B, respectively.

TABLE 1

Factor V target

| THP Concentration | Average Cq |
|---|---|
| 0 | 21.25 |
| 10 mM | 21.27 |
| 5 mM | 21.18 |
| 2 mM | 21.2 |
| 1 mM | 21.14 |
| 500 uM | 21.21 |
| 250 uM | 21.15 |
| 125 uM | 21.19 |
| 62.5 uM | 21.14 |
| 31.25 uM | 21.17 |

TABLE 2

Microglobulin target

| THP Concentration | Average Cq |
|---|---|
| 0 | 17.13 |
| 10 mM | 17.16 |
| 5 mM | 17.04 |
| 2 mM | 17.03 |
| 1 mM | 17.01 |
| 500 uM | 17.06 |
| 250 uM | 16.97 |
| 125 uM | 17.06 |
| 62.5 uM | 16.99 |
| 31.25 uM | 16.99 |

Example 2

Use of Reversible 3' Modified Nucleotides for Hot-Start PCR

Experiments were performed using reversible 3' terminated primers in hot start PCR in the presence of THP. Briefly, a 2× Master Mix containing 100 mM Tris-HCl pH8.0, 50 mM KCl, 6 mM MgCl2, 6% DMSO, 4% glycerol, 0.04% CHAPS, 0.66×SYBR Green (Life Technologies) and 50 U/µl MasterAmp Taq DNA Polymerase (Epicenter Cat # Q82250N) was prepared without addition of dNTPs to assess the amplification using modified dNTPs. For a control, 25 mM of each Standard dNTP solution (Epicenter D59104) was used. Blocked nucleotides were used at 10 µM each. Reactions were set-up with 1) standard nucleotides; 2) blocked nucleotides with THP added and 3) blocked nucleotides without addition of THP. Where appropriate, THP was added at 200 µM. Reactions included a Factor V target template at 2 ng DNA/reaction or no template controls. Half of the reactions were run as soon as possible on the ECO RealTime PCR instrument (Illumina, Inc.), while the remaining reactions were incubated at room temperature for 30 minutes and subsequently run on the instrument. The cycling conditions were; 95° C. for 2 min followed by 40 cycles of 95° C. for 15 sec/60° C. for 1 min.

Figure 4A:
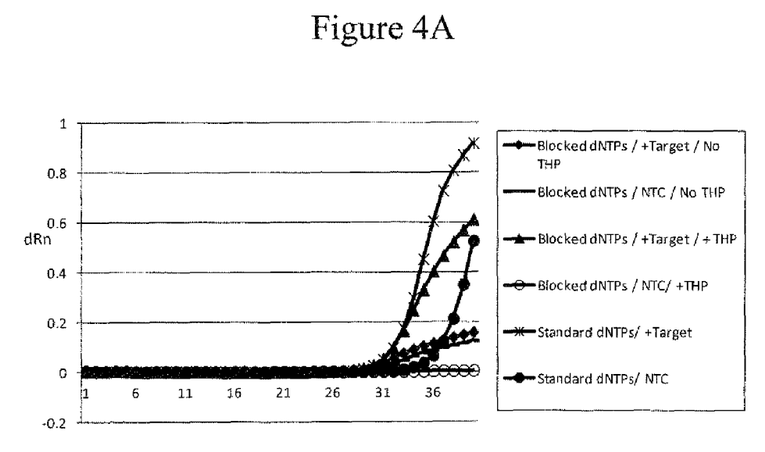
FIG. 4A is a graph showing the results of SYBR green qPCR amplification for (1) modified nucleotides, target, no THP (black diamonds); (2) modified nucleotides, no target, no THP (dashes); (3) modified nucleotides, target, plus THP (black triangles); (4) modified nucleotides, no target, plus THP (open circles); (5) standard nucleotides plus target (asterisks); and (6) standard nucleotides no target (black circles). All reactions were set up and run immediately.

FIGS. 4A and C represent exemplary amplification plots of qPCR reactions. As shown in FIG. 4A, the blocked nucleotides in the presence of target nucleic acid and THP (closed triangles) showed PCR amplification and the amplification is as robust as amplification with standard dNTPs (stars). The amplification plots for the same conditions after the reactions were incubated at room temperature for 30 min prior to assaying are shown in FIG. 4C. The NTC (No template control) reactions with blocked nucleotides and THP showed no amplification (open circles) compared to the NTC reactions of the standard nucleotides (closed circles) which show amplification occurring regardless of whether the reactions were run immediately or after 30 minutes incubation at room temperature.

Figure 4B:
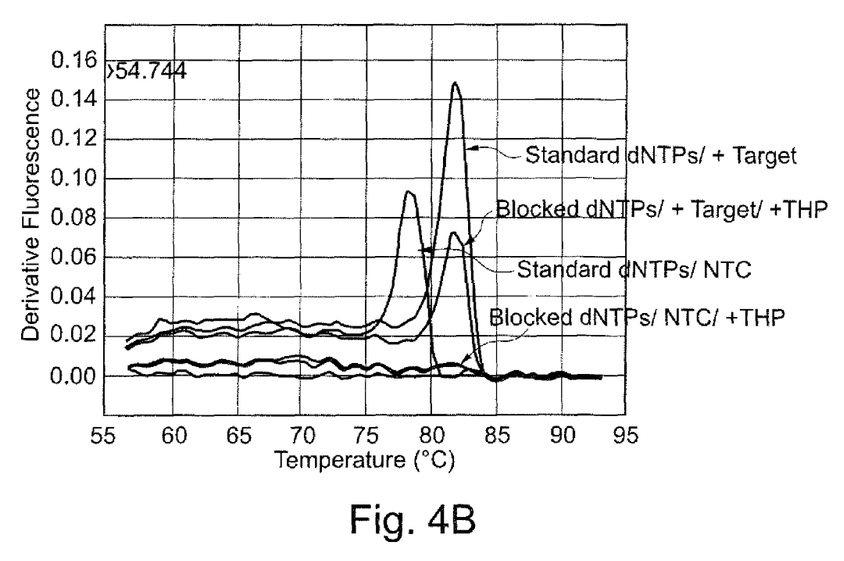
FIGS. 4B and 4D are graphs demonstrating the formation of primer-dimers using standard nucleotide primers and modified nucleotide primers in amplification experiments of 4A and 4C, respectively.
Figure 4C:
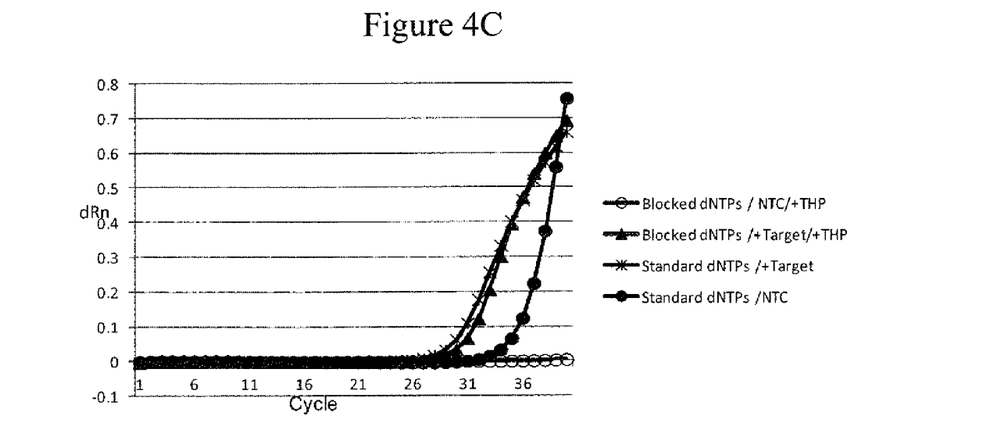
FIG. 4C is a graph showing the results of SYBR green qPCR amplification for (1) modified nucleotides, no target, plus THP (open circles); (2) modified nucleotides, target, plus THP (black circles); (3) standard nucleotides plus target (asterisks); and (4) standard nucleotides, no target (black circles). All reactions were set up, left at room temperature for 30 minutes, and then amplification was performed.
Figure 4D:
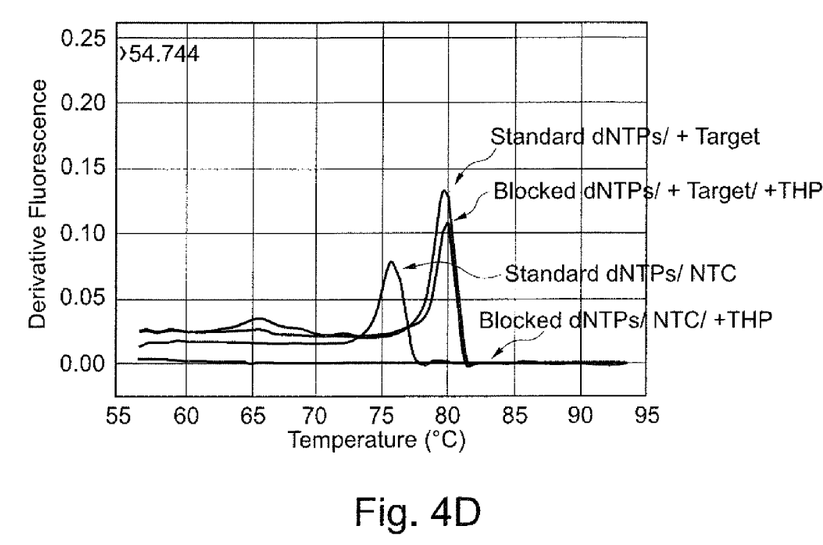

FIGS. 4B and D show melting curves for the primers used in experiments of FIGS. 4A and 4C, respectively. Regardless of whether the amplification was performed immediately after set up (FIG. 4B) or 30 minutes after set up (FIG. 4D), primer-dimers are present when standard dNTPs are used, therefore there is no hot start function using the standard dNTPs. However, primer-dimers are not present when blocked nucleotides and THP are used in the experiments, thereby demonstrating the hot start function of the methods used with blocked dNTPs.

What is claimed is:

1. A method of amplifying nucleic acids comprising:
    a) providing a nucleic acid template, an amplification enzyme, an oligonucleotide primer and a plurality of nucleotide precursors, wherein the plurality of nucleotide precursors comprises a plurality of modified nucleotides, each modified nucleotide comprising a 3' blocking group, wherein the 3' blocking group is not thermolabile;
    b) removing the 3' blocking group from the plurality of modified nucleotides in the presence of the amplification enzyme to produce a plurality of unblocked nucleotides; and
    c) amplifying the nucleic acid template using the plurality of unblocked nucleotides and the amplification enzyme present during the removing of the 3' blocking group from the plurality of modified nucleotides, wherein the amplifying the nucleic acid template comprises two or more cycles of exponential amplification of the nucleic acid template.

2. The method of claim 1, wherein the plurality comprises one type of modified nucleotide.

3. The method of claim 1, wherein the plurality comprises four types of modified nucleotides.

4. The method of claim 3, wherein the four types of modified nucleotides are dATP, dGTP, dCTP, and dTTP.

5. The method of claim 1, wherein removal of the 3' blocking group occurs in the initial denaturation step of the amplification.

6. The method of claim 1, wherein the 3' blocking group prevents polymerase extension of a primer.

7. The method of claim 1, wherein amplification occurs in the presence of primers, one or more of the primers comprising a detectable label.

8. The method of claim 1, wherein the amplification occurs in the presence of a probe.

9. The method of claim 8, wherein the probe is a fluorescent reporter probe.

10. The method of claim 9, wherein the probe is selected from the group consisting of a 5'-nuclease probe, MNAzyme probe, molecular beacon, and scorpion probe.

11. The method of claim 1, wherein the amplification occurs in the presence of a nucleic acid binding agent.

12. The method of claim 1, wherein removal of the 3' blocking group results in conversion of the 3' blocking group into a 3' hydroxyl group.

13. The method of claim 1, wherein the 3' blocking groups are removed prior to amplification.

14. The method of claim 1, wherein the 3' carbon atom of one or more of the modified nucleotides has attached a group of the structure —O—Z, wherein Z is any of —C($R^{IV}$)$_2$—O—R", —C(R')$_2$—N(R")$_2$, —C(R)$_2$—N(H)R", —C($R^{IV}$)$_2$—S—R" and —C(R)$_2$—N$_3$;
wherein —C($R^{IV}$)$_2$—O—R" is of the formula —C$R^4$($R^5$)—O—C$R^4$($R^5$)—O$R^6$ or of the formula —C$R^4$($R^5$)—O—C$R^4$($R^5$)—S$R^6$, and wherein —C($R^{IV}$)$_2$—S—R" is of the formula —C$R^4$($R^5$)—S—C$R^4$($R^5$)—O$R^6$ or of the formula —C$R^4$($R^5$)—S—C$R^4$($R^5$)—S$R^6$;
wherein each R" is or is part of a removable protecting group;
each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group, or (R')$_2$ represents an alkylidene group of formula =C(R''')$_2$ wherein each R''' may be the same or different and is selected from the group comprising hydrogen and halogen atoms and alkyl groups;
each $R^4$ and $R^5$ is independently a hydrogen atom or an alkyl group;
$R^6$ is alkyl, cycloalkyl, alkenyl, cycloalkenyl or benzyl; and
wherein said molecule may be reacted to yield an intermediate in which each R" is exchanged for H, which intermediate dissociates under aqueous conditions to afford a molecule with a free 3'OH; with the proviso that where Z is —C($R^{IV}$)$_2$—S—R", both $R^{IV}$ groups are not H.

15. The method of claim 14, wherein Z is an azidomethyl group.

16. The method of claim 14, wherein the 3' blocking group is removed with tris(hydroxymethyl)phosphine (THP).

17. The method of claim 14, wherein the 3' blocking group is removed with tris(2-carboxyethyl)phosphine.

18. The method of claim 14, wherein R' is an alkyl or substitute alkyl.

19. The method of claim 14, wherein R" is a benzyl or substituted benzyl group.

20. The method of claim 1, wherein the 3' carbon atom of the one or more modified nucleotides has attached a group of the structure —O—Z, wherein Z is selected from the group consisting of -allyl, —CR'$_2$O-allyl, —CR'$_2$NR"(allyl), —CR'$_2$NH(allyl), —CR'$_2$N(allyl)$_2$, and —CR'$_2$—S-allyl;
wherein each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy, amido group or two R' taken together represent an alkylidene group =C(R)''';
wherein R''' is selected from hydrogen, halogen, and alkyl; and
R" is a removable protecting group.

21. The method of claim 20, wherein Z is an allyl group and the blocking group removal is performed in aqueous solution with a transition metal complex comprising a transition metal and one or more phosphine ligands.

22. The method of claim 21, wherein said transition metal is selected from the group comprising platinum, palladium, rhodium, ruthenium, osmium and iridium.

23. The method of claim 21, wherein the phosphine ligands comprise derivatized triaryl phosphine ligands or derivatized trialkyl phosphine ligands.

24. The method of claim 21, wherein the phosphine ligands are derivatized with one or more functionalities selected from the group consisting of amino, hydroxyl, carboxyl and sulfonate groups.

25. The method of claim 20, wherein the blocking group is removed with a transition metal comprising a transition metal and one or more ligands selected from the group consisting of water-soluble phosphine and water-soluble nitrogen-containing phosphine ligands.

26. The method of claim 25, wherein the group of ligands comprises 3,3',3"-phosphinidynetris(benzenesulfonic acid) and tris(2-carboxyethyl)phosphines and their salts.

27. A method of amplifying a target nucleic acid comprising:
a) providing a target nucleic acid template, an amplification enzyme, a plurality of nucleotide precursors, and a pair of oligonucleotide primers, one or both of the oligonucleotide primers comprising a 3' blocking group on one or more nucleotides of the oligonucleotide primers, wherein the 3' blocking group is not thermolabile;
b) removing the 3' blocking group from the one or more nucleotides of the oligonucleotide primers in the presence of the amplification enzyme to produce unblocked oligonucleotide primers; and
c) amplifying the target nucleic acid template using the unblocked oligonucleotide primers and the amplification enzyme present during the removing of the 3' blocking group from the one or more nucleotides of the oligonucleotide primers, wherein the amplifying the nucleic acid template comprises two or more cycles of exponential amplification of the nucleic acid template.

28. The method of claim 27, wherein removal of the 3' blocking group occurs in the initial denaturation step of the amplification.

29. The method of claim 27, wherein the 3' blocking group prevents polymerase extension of the primer.

30. The method of claim 27, wherein the amplification occurs in the presence of a probe.

31. The method of claim 30, wherein the probe is a fluorescent reporter probe.

32. The method of claim 30, wherein the probe is selected from the group consisting of a 5'-nuclease probe, MNAzyme probe, molecular beacon, and scorpion probe.

33. The method of claim 27, wherein the amplification occurs in the presence of a nucleic acid binding agent.

34. The method of claim 27, wherein removal of the 3' blocking group results in conversion of the 3' blocking group into a 3' hydroxyl group.

35. The method of claim 27, wherein the 3' blocking group is removed prior to amplification.

36. The method of claim 27, wherein the 3' carbon atom of the one or more nucleotides of the oligonucleotide primer has attached a group of the structure —O—Z, wherein Z is any of —C(R$^{IV}$)$_2$—O—R", —C(R')$_2$—N(R")$_2$, —C(R')$_2$—N(H)R", —C(R$^{IV}$)$_2$—S—R" and —C(R')$_2$—N$_3$;

wherein —C(R$^{IV}$)$_2$—O—R" is of the formula —CR$^4$(R$^5$)—O—CR$^4$(R$^5$)—OR$^6$ or of the formula —CR$^4$(R$^5$)—O—CR$^4$(R$^5$)—SR$^6$, and wherein —C(R$^{IV}$)$_2$—S—R" is of the formula —CR$^4$(R$^5$)—S—CR$^4$(R$^5$)—OR$^6$ or of the formula —CR$^4$(R$^5$)—S—CR$^4$(R$^5$)—SR$^6$;

wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group, or (R')$_2$ represents an alkylidene group of formula =C(R''')$_2$ wherein each R''' may be the same or different and is selected from the group comprising hydrogen and halogen atoms and alkyl groups;

each R$^4$ and R$^5$ is independently a hydrogen atom or an alkyl group;

R$^6$ is alkyl, cycloalkyl, alkenyl, cycloalkenyl or benzyl; and wherein said molecule may be reacted to yield an intermediate in which each R" is exchanged for H, which intermediate dissociates under aqueous conditions to afford a molecule with a free 3'-OH; with the proviso that where Z is —C(R$^{IV}$)$_2$—S—R", both R$^{IV}$ groups are not H.

37. The method of claim 36, wherein Z is an azidomethyl group.

38. The method of claim 36, wherein the 3' blocking group is removed with tris(hydroxymethyl)phosphine (THP).

39. The method of claim 36, wherein the 3' blocking group is removed with tris(2-carboxyethyl)phosphine.

40. The method of claim 36, wherein R' is an alkyl or substitute alkyl.

41. The method of claim 36, wherein R" is a benzyl or substituted benzyl group.

42. The method of claim 27, wherein the 3' carbon atom of the one or more nucleotides of the oligonucleotide primers has attached a group of the structure —O—Z, wherein Z is selected from the group consisting of -allyl, —CR'$_2$O-allyl, —CR'$_2$NR"(allyl), —CR'$_2$NH(allyl), —CR'$_2$N(allyl)$_2$, and —CR'$_2$—S-allyl;

wherein each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy, amido group or two R' taken together represent an alkylidene group =C(R)''';

wherein R''' is selected from hydrogen, halogen, and alkyl; and

R" is a removable protecting group.

43. The method of claim 42, wherein Z is an allyl group and the blocking group removal is performed in aqueous solution with a transition metal complex comprising a transition metal and one or more phosphine ligands.

44. The method of claim 43, wherein said transition metal is selected from the group consisting of platinum, palladium, rhodium, ruthenium, osmium and iridium.

45. The method of claim 43, wherein the phosphine ligands comprise derivatized triaryl phosphine ligands or derivatized trialkyl phosphine ligands.

46. The method of claim 43, wherein the phosphine ligands are derivatized with one or more functionalities selected from the group consisting of amino, hydroxyl, carboxyl and sulfonate groups.

47. The method of claim 42, wherein the blocking group is removed with a transition metal comprising a transition metal and one or more ligands selected from the group consisting of water-soluble phosphine and water-soluble nitrogen-containing phosphine ligands.

48. The method of claim 47, wherein the group of ligands comprises 3,3',3"-phosphinidynetris(benzenesulfonic acid) and tris(2-carboxyethyl)phosphines and their salts.

49. The method of claim 1, further comprising repeating (a)-(c) one or more times.

50. The method of claim 27, further comprising repeating (a) (c) one or more times.

* * * * *